United States Patent [19]

Chen

[11] 4,002,697
[45] Jan. 11, 1977

[54] SELECTIVE PRODUCTION OF PARA-XYLENE

[75] Inventor: Nai Yuen Chen, Titusville, N.J.

[73] Assignee: Mobil Oil Corporation, New York, N.Y.

[22] Filed: Sept. 25, 1974

[21] Appl. No.: 509,188

Related U.S. Application Data

[63] Continuation-in-part of Ser. No. 421,459, Dec. 3, 1973, abandoned.

[52] U.S. Cl. .................. 260/671 M; 260/671 C
[51] Int. Cl.$^2$ .......................................... C07C 3/52
[58] Field of Search .......... 208/DIG. 2; 260/671 C, 260/671 M; 252/455 Z

[56] References Cited

UNITED STATES PATENTS

| | | | |
|---|---|---|---|
| 3,437,587 | 4/1969 | Ellert et al. .................... | 208/DIG. 2 |
| 3,682,996 | 8/1972 | Kerr .................................. | 252/455 |
| 3,702,886 | 11/1972 | Argauer et al. ................ | 252/455 Z |
| 3,709,979 | 1/1973 | Chu ................................. | 252/455 Z |
| 3,728,408 | 4/1973 | Tobias ............................. | 260/668 |
| 3,751,506 | 8/1973 | Burress ........................... | 260/671 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Process for the selective production of para-xylene by methylation of toluene in the presence of a catalyst comprising a crystalline aluminosilicate of average crystal size greater than 0.5 micron, which aluminosilicate has the structure of ZSM-5, ZSM-11 or ZSM-21.

15 Claims, No Drawings

SELECTIVE PRODUCTION OF PARA-XYLENE

CROSS-REFERENCE TO RELATED APPLICATIONS

This application is a continuation-in-part of copending application Ser. No. 421,459 filed Dec. 3, 1973, now abandoned.

BACKGROUND OF THE INVENTION

1. Field of the Invention

This invention relates to a process for the selective production of para-xylene by catalytic methylation of toluene in the presence of a particular crystalline aluminosilicate catalyst.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of a ZSM-5 type zeolite catalyst.

Crystalline aluminosilicate zeolites, modified by reaction with an organic substituted silane, have been described in U.S. Pat. No. 3,682,996 to Kerr and in U.S. Pat. No. 3,698,157 to Allen et al. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites modified by treatment with an organic-radical substituted silane are described, together with the use of such modified zeolites in chromatographic separation of the compounds contained in a $C_8$ aromatic feed stock.

While the above-noted prior art is considered of interest in connection with the subject matter of the present invention, the methylation process described herein utilizing the specified controlled crystal size ZSM-5 type (including zeolite ZSM-11), or ZSM-21 crystalline aluminosilicate catalyst to achieve selective production of para-xylene has not, insofar as is known, been heretofore disclosed.

Of the xylene isomers, i.e., ortho-, meta- and para-xylene, the latter is of particular value being useful in the manufacture of terephthalic acid which is an intermediate in the manufacture of synthetic fibers such as "Dacron." Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene in preference to meta- or ortho-xylene by reaction of toluene with a methylating agent in the presence of a catalyst comprising large crystals of a crystalline aluminosilicate catalyst having the structure of ZSM-5, ZSM-11 or ZSM-21.

Compared to a conventional thermodynamic equilibrium xylene mixture in which the para:meta:ortho ratio is approximately 1:2:1, the process described herein affords a xylene product having a para:meta:ortho ratio of about 9:1:1. The improved para-xylene yield reduces the cost of production and most important the cost separation of para-xylene from its isomers, which is the most expensive step in the current method employed for producing para-xylene.

The present process comprises methylation of toluene, preferably by reaction of the latter with methanol, in the presence of a particular crystalline aluminosilicate catalyst. The catalyst employed is zeolite ZSM-5, ZSM-11 or ZSM-21 which has an average crystal size greater than 0.5 micron. In a preferred embodiment, the specified zeolite of large crystal size has been modified by surface reaction with a material capable of deactivating the external surface thereof.

Such treatment involves contact of the zeolite with suitable compounds of nitrogen or silicon of a size sufficiently large as to be unable to penetrate the zeolite pore structure. A particularly preferred method of surface modification involves reaction of the zeolite with an organic radical substituted silane followed by calcination.

DESCRIPTION OF SPECIFIC EMBODIMENTS

The catalyst employed in this invention is a crystalline aluminosilicate zeolite of high silica to alumina ratio, greater than 5 and preferably greater than 30. Operative catalysts include zeolite ZSM-5 type (including zeolite ZSM-11) and zeolite ZSM-21.

Zeolite ZSM-5 is a crystalline aluminosilicate zeolite having a composition in terms of mole ratios of oxides as follows:

$$0.9 \pm 0.2\ M_{(2/n)}O : Al_2O_3 : Y\ SiO_2 : zH_2O$$

wherein M is at least one cation having a valence $n$, Y is at least 5, z is between 0 and 40. This zeolite is further characterized by a specified X-ray diffraction pattern shown below in Table I.

TABLE I

| Interplanar Spacing d(A): | Relative Intensity |
|---|---|
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 ⎫<br>     ⎬ ± 0.1<br>5.97 ⎭ | w. |
| 5.56 ± 0.1 | w. |
| 5.01 ± 0.1 | w. |
| 4.60 ± 0.08 | w. |
| 4.25 ± 0.08 | w. |
| 3.85 ± 0.07 | v.s. |
| 3.71 ± 0.05 | s. |
| 3.04 ± 0.03 | w. |
| 2.99 ± 0.02 | w. |

TABLE I-continued

| Interplanar Spacing d(A): | Relative Intensity |
|---|---|
| 2.94 ± 0.02 | w. |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/I$_o$, where I$_o$ is the intensity of the strongest line or peak, and d(obs.), the interplanar spacing in A, corresponding to the recorded lines, were calculated. In Table I the relative intensities are given in terms of the symbols s. = strong, w. = weak and v.s. = very strong. It should be understood that this X-ray diffraction pattern is characteristic of all the species of ZSM-5 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it had been subjected to thermal treatment.

Zeolite ZSM-5 and its preparation are more particularly described in U.S. Pat. No. 3,702,886 the disclosure of which is incorporated herein by reference.

Zeolite ZSM-11, here considered as a member of the group designated "ZSM-5 type" is described in U.S. Pat. No. 3,709,979.

Preparation of synthetic zeolite ZSM-21 is typically accomplished as follows: A first solution comprising 3.3 g. sodium aluminate (41.8% Al$_2$O$_3$, 31.6% Na$_2$O and 24.9% H$_2$O), 87.0 g. H$_2$O and 0.34 g. NaOH (50% solution with water) was prepared. The organic material pyrrolidine was added to the first solution in 18.2 g. quantity to form a second solution. Thereupon, 82.4 g. colloidal silica (29.5% SiO$_2$ and 70.5% H$_2$O) was added to the second solution and mixed until a homogeneous gel was formed. This gel was composed of the following components in mole ratios:

| | |
|---|---|
| $\frac{R^+}{R^+ + M^+}$ | 0.87, wherein M is sodium and R is the pyrrolidine ion. |
| $\frac{OH^-}{SiO_2}$ | 0.094 (Not including any contribution of OH$^-$ from pyrrolidine) |
| $\frac{H_2O}{OH^-}$ | 210 (Not including any contribution of OH$^-$ from pyrrolidine) |
| $\frac{SiO_2}{Al_2O_3}$ | 30.0 |

The mixture was maintained at 276° C. for 17 days, during which time crystallization was complete. The product crystals were filtered out of solution and water washed for approximately 16 hours on a continuous wash line.

X-ray analysis of the crystalline product proved the crystals to have a diffraction pattern as shown in Table I.

TABLE I

| d (A) | I/Io |
|---|---|
| 9.5 ± 0.30 | Very Strong |
| 7.0 ± 0.20 | Medium |
| 6.6 ± 0.10 | Medium |
| 5.8 ± 0.10 | Weak |
| 4.95 ± 0.10 | Weak |
| 3.98 ± 0.07 | Strong |
| 3.80 ± 0.07 | Strong |
| 3.53 ± 0.06 | Very Strong |
| 3.47 ± 0.05 | Very Strong |
| 3.13 ± 0.05 | Weak |
| 2.92 ± 0.05 | Weak |

Chemical analysis of the crystalline product led to the following compositional figures:

| Composition | Wt.% | Mole Ratio on Al$_2$O$_3$ Basis |
|---|---|---|
| N | 1.87 | — |
| Na | 0.25 | — |
| Al$_2$O$_3$ | 5.15 | 1.0 |
| SiO$_2$ | 90.7 | 29.9 |
| N$_2$O | — | 1.54 |
| Na$_2$O | — | 0.11 |
| H$_2$O | — | 9.90 |

Physical analysis of the crystalline product calcined 16 hours at 1000° F. showed it to have a surface area of 304 m$^2$/g and adsorption tests produced the following results:

| Adsorption | Wt.% |
|---|---|
| Cyclohexane | 1.0 |
| n-Hexane | 5.4 |
| Water | 9.0 |

In determining the sorptive capacities, a weighed sample of zeolite was heated to 600° C. and held at that temperature until the evolution of basic nitrogeneous gases ceased. The zeolite was then cooled and the sorption test run at 12 mm for water and 20 mm for hydrocarbons.

Zeolite ZSM-21 is the subject of copending application Ser. No. 358,192, filed May 7, 1973.

These catalysts are characterized by unusually high stability and by exceptional selectivity in hydrocarbon reactions generally and especially in reactions of aromatic hydrocarbons.

It is a particular feature of the process of this invention that the average crystal size of the selected zeolite employed be greater than 0.5 micron in diameter and generally in the approximate range of 0.5 to 10 microns and preferably between about 1 and about 8 microns. Without being limited by any theory, the criticality of crystal size would seem to be attributable to the selective production of p-xylene as a result of a balance between the relative rate of diffusion of the xylene isomers and the rate of alkylation. It is postulated that when the latter rate is much faster than the diffusion rate, p-xylene would be the predominant product. Techniques utilized to obtain zeolite crystals within the foregoing ranges involve reaction of sources of alumina, silica and appropriate sodium compounds. For example, for ZSM-5, reaction of a solution of sodium silicate, aluminum sulfate, sodium chloride and sulfuric acid with tri-n-propylamine and n-propyl bromide.

The zeolite of requisite crystal size is converted from its as synthesized alkali metal form to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups I-B to VIII of the Periodic Table including by way of example, nickel, zinc or rare earth metals.

The crystals of zeolite in a form substantially free of alkali metal, i.e., containing less than 1.5 weight percent alkali metal, are then contacted with a surface modifying agent capable of deactivating catalytic sites located on the external surface of the zeolite. Treatment involves contact with a suitable compound of silicon or nitrogen of a size sufficiently large as to be unable to penetrate the zeolite pore structure. Representative of such compounds are: phenyl carbazole, dimethyl dichloro silane, bis-(tri-methylsilyl)-acetamide, trimethyl chlorosilane and hexamethyl disilazane, substituted phenyl carbazole, such as alkyl phenyl carbazole, N-phenyl, acridine, substituted phenyl acridines, such as alkyl phenyl acridine, N-phenyl phenoxazine, 3-[2-pyridyl]-5,6-diphenyl-1,2,4-triazine and 1,4-di-p-toluidino-5-hydroxy anthraquinone. A particular feasible method of surface modification involves reaction of the zeolite with an organic radical substituted silane and subsequent calcination.

Organic substituted silanes useful in preparing the modified zeolites utilized in the present process are those having the general formula:

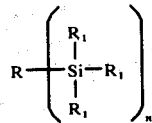

where $n$ is 1 or 2 and R is a reactive group such as hydrogen, alkoxy, halogen, carboxy, amino, acetamide and $R_1$ can be the same group as R or an organic radical which may include alkyl of from 1 up to about 40 carbon atoms, alkyl or aryl carboxylic acid wherein the organic portion of the alkyl group contains about 1 to 30 carbon atoms and the aryl group contains about 6 to 24 carbon atoms, aryl groups of about 6 to 24 carbons, which may be further substituted, alkaryl and aralkyl groups containing about 7 up to about 30 carbon atoms. Preferably, the alkyl group of an alkyl silane is between 1 and 4 carbon atoms in chain length. Mixtures of the above compounds may likewise be used and may, in fact, be preferable from a commercial standpoint.

The selected silane and large crystal size zeolite of low alkali metal content are contacted at an elevated temperature. Generally, the silane and zeolite are contacted on a weight basis of about 2 percent to about 200 percent of zeolite and preferably about 10 to about 100 percent, respectively. The amount of silane should desirably be such as to achieve about 1 to about 5 weight percent of silicon bonded to the outer surface of the zeolite. It is also preferable that a binder for the zeolite be employed, such as for example bentonite. For good contact between the reactants, it is also preferable to employ a reaction medium. Satisfactory reaction media include the ethers, aliphatic hydrocarbons and halo-substituted aliphatic hydrocarbons of 5 to about 8 carbon atoms, aromatic, halo-substituted aromatic hydrocarbons and nitrogen containing compounds such as heterocyclics. A particularly preferred media is pyridine.

An elevated temperature, generally between about 75° C. and about 200° C., should be employed for the reaction. Usually, the reactants are charged to the medium and heated at the reflux point of the system for about 1 to 10 hours. The mixture is then contacted with a volatile solvent such as chloroform or n-pentane, filtered and dried in an oven at a temperature of about 75° to 125° C. The resulting modified zeolite is considered to have the organic-substituted silane chemically bonded thereto.

Prior to use, the silane-modified zeolite is calcined in an inert atmosphere, e.g., helium or in an oxygen-containing atmosphere, e.g., air. Calcination takes place at a temperature in the approximate range of 300° to 700° C. and preferably between 450° and 550° C.

In practicing the desired methylation process it may be desirable to incorporate the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite. A particularly suitable combination is one containing about 65 weight percent of the zeolite in 35 weight percent of a relatively inactive alumina matrix.

Methylation of toluene in the presence of the above-described catalyst of specified zeolite of average crystal size greater than 0.5 micron is effected by contact of the toluene with a methylating agent, preferably methanol, at a temperature between about 300° and about 700° C. and preferably between about 400° and about 500° C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. A weight hourly space velocity of between about 0.5 and about 10 is employed. The molar ratio of methylating agent to toluene is generally between about 0.5 and about 5. When methanol is employed as the methylating agent a suitable molar ratio of methanol to toluene has been found to be approximately 0.5–2 moles of methanol per mole of toluene. With the use of other methylating agents, such as methylchloride, methylbromide, dimethylether or dimethylsulfide, the molar ratio of methylating agent to toluene may vary within the aforenoted range. Reaction is suitably accomplished utilizing a weight hourly space velocity of between about 0.5 and about 30 and preferably between about 1 and about 10. The reaction product consisting predominantly of para-xylene, together with comparatively smaller amounts of meta-xylene and ortho-xylene may be separated by any suitable means, such as by passing the same through a water condenser and subsequently passing the organic phase through a column in which chromatographic separation of the xylene isomers is accomplished.

The following examples will serve to illustrate the process of this invention without limiting the same:

EXAMPLES 1–5

ZSM-5 crystals of 3 × 7 micron size were obtained using the following reactants:

| Silicate Solution | |
|---|---|
| 42.2 lb. | Q Brand Sodium Silicate ($Na_2O/SiO_2 = 3.3$) |
| 52.8 lb. | Water |
| Acid Solution | |
| 612 grams | Aluminum Sulfate |
| 1600 grams | Sulfuric Acid |
| 7190 grams | Sodium Chloride |
| 72.2 lb. | Water |
| Organics | |
| 1290 grams | Tri-n-propylamine |
| 1110 grams | n-Propylbromide |

The silicate solution and acid solution were nozzle mixed to form a gelatinous precipitate that was charged to a 30 gallon stirred autoclave. When gelation was complete the organics were added and the temperature raised to 315° F. with agitation. The reaction mixture was held at 315° F. with an agitation rate of 121 RPM for 17 hours. The product at this time was analyzed by X-ray diffraction and was reported to be ZSM-5. The product was then washed free of soluble salts and dried. Analysis of the product gave the following in terms of mole ratios:

| | |
|---|---|
| $Al_2O_3$ | 1.0 |
| $SiO_2$ | 74.4 |
| $Na_2O$ | 0.31 |
| N | 2.26 |
| C | 21.9 |

The ZSM-5 so prepared was precalcined in air at 370° C. and thereafter ammonium exchanged by contacting twice with 5N $NH_4Cl$ solution at 100° C. (15 ml. per gram zeolite), once for 16 hours, the second time for 4 hours, filtered, washed free of chloride and air dried.

The resulting ammonium form of ZSM-5 was converted to the hydrogen form by calcination in air at 1° C./minute to 538° C. and then held at 538° C. for 10 hours.

Silane treatment of the HZSM-5 so obtained was carried out in reflux pyridine with dimethyl dichlorosilane (8 grams of zeolite, 50 cc of pyridine, 10 cc of dimethyl dichlorosilane) for 2 hours. The product was then filtered while hot, washed with pyridine (100 cc), chloroform (100 cc) and n-pentane (100 cc), pelleted and screened to 30/50 mesh.

A 0.5 gram sample was loaded into a reactor, heated in flowing helium at 200° C. overnight and the temperature was then raised to 500° C. for 30 minutes before use in the methylation run.

Runs were made at 500° C. by passing a liquid feed containing methanol/toluene (2/1 molar ratio) over the catalyst. The reactor effluent passed through a water condenser and a two-phase liquid product collected. For the organic phase, a 35 foot 10% polyphenyl ether on gas chrom R column was used. The column was held at 95° C. until the appearance of o-xylene peak and the temperature was then raised at 8° C./min. to 180° C. and held for 30 minutes. A summary of the experimental results for Examples 1–5 is presented in Table II below.

TABLE II

| Example | 1 | 2 | 3 | 4 | 5 |
|---|---|---|---|---|---|
| Sample on Stream Time, hr. | 0.5–0.8 | 1.0–1.5 | 2.0–3.0 | 0.5–1.5 | 3.0–4.0 |
| WHSV | 6.6 | 16.4 | 6.6 | 6.6 | 6.6 |
| Temperature, ° C. | 500 | 500 | 500 | 500 | 500 |
| Methanol/Toluene, mol. | 2 | 2 | 2 | 2 | 2 |
| Composition, Organic Phase $C_6^-$ | 2.4 | 2.8 | 5.1 | 3.5 | 6.7 |
| Benzene | 0.5 | 0.1 | 0.1 | 0.1 | 0 |
| Toluene | 61.0 | 70.8 | 63.9 | 61.1 | 73.6 |
| p-Xylene | 23.0 | 19.3 | 15.2 | 23.0 | 8.2 |
| m-Xylene | 6.8 | 2.3 | 5.0 | 5.3 | 3.8 |
| o-Xylene | 2.7 | 2.2 | 5.5 | 2.6 | 4.2 |
| Ethyl benzene | — | — | — | — | — |
| Trimethyl benzenes | 3.6 | 2.5 | 5.2 | 4.4 | 3.6 |
| % Toluene Methylated | 33.5 | 24.2 | 29.2 | 33.0 | 18.8 |
| % Xylene as | | | | | |
| para | 71 | 81 | 59 | 74 | 51 |
| meta | 21 | 10 | 19 | 17 | 23 |
| ortho | 8 | 9 | 22 | 8 | 26 |

From the above results, it will be seen that the equilibrium xylene isomer mixture of 23 percent para, 51 percent meta and 26 percent ortho has been improved to a percentage ratio of 81 percent para, 10 percent meta and 9 percent ortho as a result of toluene methylation conducted in the presence of large crystals of HZSM-5 modified by surface silylation with a large silane compound unable to penetrate the intracrystalline pores and subsequent calcination. It is of further interest to note that as the reaction severity increased, the meta/ortho changed from 1/1 to 2/1 approaching the equilibrium value, while the para isomer remained in high concentration.

EXAMPLES 6–8

ZSM-5 crystals of < 0.1 micron size were obtained using the following reactants:

| Solution A | |
|---|---|
| 858 grams | Sodium Aluminate |
| 58 grams | Sodium Hydroxide |
| 50 lb. | Water |
| Solution B | |
| 160 lb. | Q-Brand Sodium Silicate ($Na_2O/SiO_2 = 3.3$) |
| 200 lb. | Water |
| Solution C | |
| 20 lb. | tetrapropylammonium bromide |
| 100 lb. | Water |
| Solution D | |
| 16 lb. | Sulfuric Acid |
| 50 lb. | Water |
| Solution E | |
| 60 lb. | Sodium Chloride |
| 72 lb. | Water |

Solution B was combined with Solution C and the resultant solution combined with Solution A. To this mixture was added 480 grams of zeolite ZSM-5 seed crystals. Then the mixture was mixed with Solution D through a mixing nozzle to form a gelatinous precipitate that was discharged into 150 gallon jacketed kettle. After the gel was charged, solution E was added and the mixture thoroughly blended. The reaction mixture was heated with agitation to 210° F. and held for 6 days. The agitation rate was about 30 RPM. The product after 6 days was analyzed by X-ray diffraction and found to be 100 percent ZSM-5. The product was washed free of soluble salts and dried. Analysis of the product gave the following in terms of mole ratios:

| | |
|---|---|
| $Al_2O_3$ | 1.0 |
| $SiO_2$ | 67.7 |
| $Na_2O$ | 0.81 |
| N | 1.31 |

The ZSM-5 so prepared was precalcined in air at 370° C. and thereafter ammonium exchanged, converted to the hydrogen form and silane treated as described above in Examples 1–5.

Methylation of toluene with methanol using the silylated ZSM-5 was carried out at 300°, 400° and 500° C. in the manner described in the previous examples. A summary of the experimental results for these examples is shown in Table III below:

TABLE III

| Example | 6 | 7 | 8 |
|---|---|---|---|
| Sample on Stream Time, Hr. | 0.5–1.5 | 2.0–3.0 | 3.5–4.5 |
| WHSV | 6.6 | 6.6 | 6.6 |
| Temperature, ° C. | 400 | 300 | 500 |
| Methanol/Toluene, mol. | 2 | 2 | 2 |
| Composition, Organic Phase $C_6^-$ | 8.0 | 6.9 | 4.4 |
| Benzene | 0 | 0 | 0 |
| Toluene | 35.2 | 73.0 | 27.5 |
| p-Xylene | 9.6 | 4.2 | 11.9 |
| m-Xylene | 15.9 | 3.8 | 24.5 |
| o-Xylene | 11.0 | 8.1 | 10.4 |
| Ethyl benzene | — | — | — |
| Trimethyl benzenes | 20.2 | 4.0 | 21.4 |
| % Toluene Methylated | 56.2 | 22.5 | 62.0 |
| % Xylene as | | | |
| para | 26 | 26 | 25 |
| meta | 44 | 24 | 52 |

TABLE III-continued

| Example | 6 | 7 | 8 |
|---|---|---|---|
| ortho | 30 | 50 | 23 |

From the above results, it will be evident that with the use of silylated small crystallites of HZSM-5 in methylation of toluene, the isomer distribution at 500° C. did not appreciably change from that of the equilibrium mixture. It is further evident that the use of small crystals, i.e., < 0.1 micron did not afford the desired selective production of para-xylene achieved with the process of the invention.

EXAMPLES 9–12

These examples serve to illustrate the marked difference observed in methylating toluene utilizing ZSM-5 crystals of 3 × 7 micron size compared with use of ZSM-5 crystals of < 0.1 micron size.

The larger ZSM-5 crystals were prepared, ammonium exchanged and calcined as described in Examples 1–5 to yield HZSM-5. The smaller ZSM-5 crystals were prepared, ammonium exchanged and calcined as described in Examples 6–8 to yield the hydrogen form.

Methylation of toluene with methanol using these ZSM-5 catalysts was carried out in the manner described in the previous examples. A summary of the experimental results for these examples is shown in Table IV below.

TABLE IV

| Example | 9 | 10 | 11 | 12 |
|---|---|---|---|---|
| Crystallite Size | 3 × 7 microns | 3 × 7 microns | < 0.1 microns | < 0.1 microns |
| Temp. ° C | 400 | 500 | 260 | 425 |
| WHSV | 6.6 | 6.6 | 4 | 8 |
| Toluene alkylated, Wt. % | 18.8 | 39.2 | 22.6 | 49.0 |
| % Xylenes as | | | | |
| Para | 48 | 46 | 25 | 24 |
| Meta | 30 | 36 | 26 | 49 |
| Ortho | 22 | 18 | 49 | 27 |
| Trimethyl benzenes/ Xylenes | .35 | .10 | 0.78 | 0.50 |

It will be evident from the above results that the use of large zeolite crystals, i.e., 3 × 7 micron size, afforded considerably greater yield of p-xylene than the small crystals, i.e., < 0.1 micron size. Moreover, the ratio of para isomer to ortho isomer increased from 1:2 to 2–2.5:1. This ratio using the larger crystal size zeolite thus exceeded the thermodynamic ratio (1:1) providing strong indication that shape selective alkylation reactions were taking place within the intracrystalline cavities of the zeolite.

EXAMPLES 13–16

ZSM-21 crystals of < 0.3 micron size were obtained using the following reactants:
A. Aluminate Solution
330 g. $NaAlO_2$ (43.1% $Al_2O_3$, 33.1 wt. % $Na_2O$)
3.4 g. 50% NaOH solution
870 g. $H_2O$
B. Silica Solution
824 g. Ludox (30% $SiO_2$)
C. 182 g. Pyrrolidine These solutions were mixed together adding solution C to solution A, mixing, then adding solution B and mixing rapidly for 10 minutes. These solutions were mixed directly in a 2 liter stirred autoclave then heated to and held at 135° C. for 17 days until the crystalline product was obtained. The crystalline product was separated from the crystallizing mixture by filtration and washing.

By X-ray analysis the product was shown to be ZSM-21.

The calcined product by analysis had the following composition:

| | |
|---|---|
| SiO$_2$ | 91.1 wt. % |
| Al$_2$O$_3$ | 5.33 wt. % |
| Na | 0.19 wt. % |

Sorptive properties were as follows:

| | |
|---|---|
| Cyclohexane | 2.1 wt. % |
| n-hexane | 8.2 wt. % |
| H$_2$O | 11 wt. % |

The surface area was 349 m$^2$/g.

Methylation of toluene with methanol using the above prepared ZSM-21 was carried out utilizing a mole ratio of methanol/toluene of 0.5 in the manner described in the previous examples. A summary of the experimental results for these examples is shown in Table V below.

TABLE V

| Example | 13 | 14 | 15 | 16 |
|---|---|---|---|---|
| Pressure, psig | 400 | 400 | 400 | 14.7 |
| Sample On-Stream Time, Hr. | 23.2 | 24.8 | 27.5 | 49.7 |
| WHSV | 8 | 8 | 4 | 4 |
| Temperature, ° C. | 343 | 400 | 400 | 343 |
| Composition, Organic Phase | | | | |
| C$_6^-$ (including benzene) | 0.2 | 1.3 | 1.7 | 0 |
| Toluene | 75.7 | 66.0 | 67.3 | 84.5 |
| p-xylene | 3.8 | 5.2 | 5.0 | 3.3 |
| m-xylene | 8.8 | 11.3 | 11.2 | 3.6 |
| o-xylene | 3.7 | 4.8 | 4.5 | 5.6 |
| Trimethyl benzenes | 7.6 | 10.9 | 9.6 | 2.8 |
| % Toluene Methylated | 23.9 | 32.2 | 30.3 | 15.3 |
| % Xylene as | | | | |
| para | 23 | 24 | 24 | 27 |
| meta | 54 | 53 | 54 | 29 |
| ortho | 23 | 23 | 22 | 44 |

It is evident, from the above results, that the desired selective production of para-xylene was not achieved with crystals of < 0.3 micron in size. It is further to be noted that at 400 psig, the isomers of xylene were close to the composition at equilibrium; while at atmosphere pressure, the isomer distribution was controlled by the kinetics of the alkylation reaction favoring the ortho isomer.

EXAMPLES 17–18

ZSM-21 crystals of 1–4 micron size were obtained using the following reactants:

A. Silicate Solution
    101.6 g. Q-Brand Silicate (28.8 wt.% SiO$_2$, 8.9 wt.% Na$_2$O)
    6.5 g. 50% NaOH solution
    59.8 g. H$_2$O
B. Acid Alum Solution
    19.4 g. Al$_2$(SO$_4$)$_3$·18H$_2$O
    4.5 g. H$_2$SO$_4$
    174 g. H$_2$O -continued C. Ethylenediamine 30.0 g.

These solutions were mixed together adding solution C to solution A then adding solution B and mixing vigorously for 15 minutes. The mixture was charged to a polypropylene jar and sealed. This was held for 62 days at 210° F. in a non-stirred state to allow the product to crystallize.

The solid crystalline product was filtered from the slurry and water washed to remove unreacted soluble components and then dried at 230° F.

X-ray analyses established the material as ZSM-21. Product analysis on dried sample were as follows:

| | |
|---|---|
| N | 3.09 wt. % |
| Na | 0.07 wt. % |
| Al$_2$O$_3$ | 10.1 wt. % |
| SiO$_2$ | 85.2 wt. % |
| Solids | 88.4 wt. % |

Sorptive properties after calcination 16 hours at 1000° F. were:

| | |
|---|---|
| Cyclohexane | 2.2 wt. % |
| n-Hexane | 5.3 wt. % |
| H$_2$O | 13.9 wt. % |

The surface area was 347 m$^2$/g.

Methylation of toluene with methanol using the above prepared ZSM-21 was carried out employing a mole ratio of methanol/toluene of 0.5 in the manner described hereinabove. A summary of the experimental results for these examples is shown in Table VI below.

TABLE VI

| Example | 17 | 18 |
|---|---|---|
| Pressure, psig | 400 | 400 |
| Sample On-Stream Time, Hr. | 1.5 | 7.0 |
| WHSV | 8 | 8 |
| Temperature ° C. | 400 | 426 |
| Composition, Organic Phase | | |
| C$_6^-$ (including benzene) | 0 | 0 |
| Toluene | 87.0 | 94.2 |
| p-xylene | 4.3 | 1.7 |
| m-xylene | 2.9 | 1.3 |
| o-xylene | 4.3 | 2.3 |
| Trimethyl benzenes | 1.4 | 0.4 |
| % Toluene Methylated | 12.9 | 5.7 |
| % Xylene as | | |

TABLE VI-continued

| Example | 17 | 18 |
|---|---|---|
| para | 38 | 32 |
| meta | 25 | 25 |
| ortho | 37 | 43 |

It will be seen from the above data that by increasing the size of the crystals of ZSM-21 from < 0.3 micron to 1–4 micron, the selectivity for p-xylene increased 33 to 65%. The concentration of p-xylene in each instance exceeded its equilibrium value.

EXAMPLES 19–20

The ammonium form of ZSM-5 crystals of 3 × 7 micron size prepared according to Example 1 is calcined at about 1000° F. for 16 hours. Three grams of the calcined material is exchanged with 35 ml. of a 0.5N 2.9/1 zinc chloride/ammonium chloride solution at 110° F. for 4 hours. The material is then washed with water and dried in air to yield a catalyst having a zinc concentration of about 0.5 weight percent and a sodium content of about 0.1 weight percent.

Methylation of toluene is carried out with methyl chloride by passing a mole ratio of 1:1 of toluene and gaseous methyl chloride over the catalyst at a pressure of 1 atmosphere and a temperature of 400° to 500° C. A summary of the experimental results is shown in Table VII below.

TABLE VII

| Example | 19 | 20 |
|---|---|---|
| Temperature ° C. | 500 | 400 |
| WHSV | 8 | 8 |
| % Toluene Methylated | 45 | 20 |
| % Xylene as | | |
| para | 48 | 50 |
| meta | 35 | 25 |
| ortho | 17 | 25 |

EXAMPLE 21

Five grams of ZSM-21 having a crystal size of 1–4 micron and prepared as in Example 17 are mixed with 2 grams of N-phenyl acridine. The mixture is loaded in a microreactor and heated to 300° C. in flowing hydrogen for 30 minutes to deactivate the external surface activity. By deactivating the surface activity, the selectivity of p-xylene is improved from 32–38 percent to over 40 percent.

EXAMPLE 22

Three grams of HZSM-5 of 3 × 7 micron size prepared as in Examples 1–5 are treated by immersing in a 2% phenyl carbazole solution in acetone for 30 minutes, filtered and air dried at 100° C. The catalyst is loaded in a microreactor and heated to 300° C. in flowing hydrogen for 30 minutes. Thereafter, a feedstock consisting of a 1:1 molal ratio of toluene:methanol is passed over the catalyst at 1 LHSV and 300° C. Twenty percent of the toluene is alkylated. Among the xylenes produced, 60% is para, 20% is meta and 20% is ortho.

EXAMPLES 23–24

These examples illustrate an alternate method of introducing nitrogen poison to the zeolite catalyst.

In a separate experiment, a catalyst of HZSM-5 of 3 × 7 micron size prepared as in Examples 1–5 is tested under the conditions of Example 22. After 1 hour on-stream, the feedstock of toluene and methanol is switched from a pure mixture to one containing 1000 ppm of dissolved phenyl carbazole and the reaction continued. A summary of the results is shown in Table VIII below.

TABLE VIII

| Example | 23 | 24 |
|---|---|---|
| On-Stream Time | 30 minutes | 1.5 hours |
| LHSV | 1 | 1 |
| Temperature ° C. | 300 | 300 |
| % Toluene Methylated | 25 | 18 |
| % Xylene as | | |
| para | 48 | 60 |
| meta | 17 | 20 |
| ortho | 35 | 20 |
| Trimethylbenzenes/Xylenes | .35 | .10 |

It is seen from the above results that the selectivity for p-xylene is improved with the addition of the nitrogen poison and that the yield of trimethylbenzene also decreased.

EXAMPLES 25–26

A catalyst of HZSM-11 of 3 × 7 micron size is used for methylating toluene with methanol as described in Examples 9–10 with the following results:

TABLE IX

| Example | 25 | 26 |
|---|---|---|
| Temperature ° C. | 400 | 500 |
| WHSV | 6.5 | 6.5 |
| % Toluene Methylated | 19 | 40 |
| % Xylene as | | |
| para | 47 | 45 |
| meta | 32 | 37 |
| ortho | 21 | 18 |

It is to be understood that the foregoing description is merely illustrative of preferred embodiments of the invention of which many variations may be made by those skilled in the art within the scope of the following claims without departing from the spirit thereof.

I claim:

1. In a process for manufacture of xylene by reacting toluene with a methylating agent in the presence of a crystalline aluminosilicate catalyst, the improvement resulting in a proportion of p-xylene greater than the thermo dynamic equilibrium proportion of total xylenes which comprises conducting the reaction in the presence of catalyst particles of ZSM-5, ZSM-11 or ZSM-21 of average crystal size greater than 0.5 micron, said catalyst particles having been surface deactivated by reaction with a compound of nitrogen or silicon of a size sufficiently large as to be unable to penetrate the pore structure of said crystalline aluminosilicate.

2. The process of claim 1 wherein said methylating agent is methanol, methylchloride, methylbromide, dimethylether or dimethylsulfide.

3. The process of claim 1 wherein said crystal size is in the approximate range of 0.5 to 10 microns.

4. The process of claim 1 wherein said crystal size is within the approximate range of 1 to 8 microns.

5. The process of claim 1 wherein the surface of said catalyst has been modified by silylation with a silane incapable of entering the pores of said crystalline aluminosilicate followed by calcination.

6. The process of claim 5 wherein said silane is dimethyldichlorosilane.

7. The process of claim 5 wherein said calcination is carried out at a temperature between about 300° C. and about 700° C.

8. The process of claim 1 wherein said nitrogen compound is phenyl carbazole.

9. The process of claim 1 wherein the step of reacting toluene with a methylating agent is carried out at a temperature between about 300° C. and about 700° C., a pressure of between about 1 atmosphere and about 1000 psig, a weight hourly space velocity of between about 0.5 and about 10 employing a molar ratio of methylating agent to toluene of between about 0.5 and about 5.

10. The process of claim 5 wherein said silylation is effected at a temperature of between about 75° C. and about 200° C. the silane and zeolite being contacted on a weight basis of about 2 percent to about 200 percent of zeolite.

11. The process of claim 1 wherein said crystalline aluminosilicate is characterized by a silica/alumina ratio in excess of 30.

12. The process of claim 1 wherein the crystalline aluminosilicate catalyst is ZSM-5.

13. The process of claim 1 wherein the crystalline aluminosilicate is ZSM-11.

14. The process of claim 1 wherein the crystalline aluminosilicate is ZSM-21.

15. The process of claim 5 wherein the crystalline aluminosilicate catalyst is ZSM-5.

* * * * *